US006419133B1

(12) United States Patent
Grose

(10) Patent No.: US 6,419,133 B1
(45) Date of Patent: Jul. 16, 2002

(54) STETHOSCOPE CARRIER

(76) Inventor: Craig M. Grose, 267 Chimesview Dr., South Ogden, UT (US) 84405

( * ) Notice: Subject to any disclaimer, the term of this patent is extended or adjusted under 35 U.S.C. 154(b) by 936 days.

(21) Appl. No.: 08/620,427

(22) Filed: Mar. 6, 1996

(51) Int. Cl.[7] ............................................. A45C 11/00
(52) U.S. Cl. ...................................................... 224/269
(58) Field of Search ................................ 224/269, 678; 181/131

(56) References Cited

U.S. PATENT DOCUMENTS

| | | | | |
|---|---|---|---|---|
| 2,804,969 A | * | 9/1957 | Bernett | 181/131 X |
| 3,797,717 A | * | 3/1974 | Collins | 224/231 |
| 5,172,683 A | * | 12/1992 | West | 224/610 X |
| 5,221,032 A | * | 6/1993 | Bott et al. | 224/678 X |
| 5,451,725 A | * | 9/1995 | Goldman | 224/269 X |
| D375,161 S | * | 10/1996 | Hart | D24/134 |
| 5,692,657 A | * | 12/1997 | Kilo et al. | 224/269 |

* cited by examiner

Primary Examiner—Renee Luebke
(74) Attorney, Agent, or Firm—Thompson E. Fehr

(57) ABSTRACT

A stethoscope carrier has a stethoscope bell receiver space formed by anteriorly protruding bell receiver flanges and a recessed bell retaining collar; a pair of ear piece retaining grooves together with a set of ear piece retaining groove keepers located laterally on the carrier; a set of stethoscope tubing retainers consisting of an arched tubing shelf/retainer and side tubing retainers; and, optionally, a waist clip forming the most posterior aspect of the carrier. The stethoscope bell receiver space and ear piece retaining grooves are precisely sized to receive and protectively store and release the bell and ear pieces of a stethoscope in a slip-fit relationship. The stethoscope tubing retainers allow the excess stethoscope tubing to be wrapped around the carrier. Lastly, the waist clip provides a means for securing the carrier as a whole.

10 Claims, 1 Drawing Sheet

STETHOSCOPE CARRIER

BACKGROUND OF THE INVENTION

1. Field of the Invention

This invention relates to carriers/holsters, more specifically to a stethoscope carrier.

2. Description of the Related Art

For years, medical personnel have used stethoscopes as an integral part of patient examination and evaluation. Stethoscope users have continually been faced with the problem of having no convenient way to carry or store their stethoscope. If the stethoscope were put in a lab coat pocket, the tubing could catch, pulling the stethoscope from the pocket or tearing the coat. If the stethoscope were hung around one's neck, the stethoscope could easily fall, injuring the patient, or catch and injure the person transporting the stethoscope, thereby causing frustration for both the patient and the health care provider.

Moreover, many expensive stethoscopes have been lost, forgotten, or damaged for no reason other than the inherent ungainly, inconvenient nature of the stethoscope, itself.

These problems have so far not been effectively addressed.

SUMMARY OF THE INVENTION

The objects and advantages of the present invention are:

(a) to provide a convenient way safely to carry an inherently awkward instrument, viz., the stethoscope;

(b) to provide a safe means of storage for the stethoscope in order to reduce the risk of loss of, or damage to, the stethoscope; and (c) to provide an inexpensive carrier system for stethoscopes which will be available to all health care providers.

Further objects and advantages of the present invention will become apparent from a consideration of the drawings and ensuing description.

DESCRIPTION OF THE PREFERRED EMBODIMENT

Figure 1:
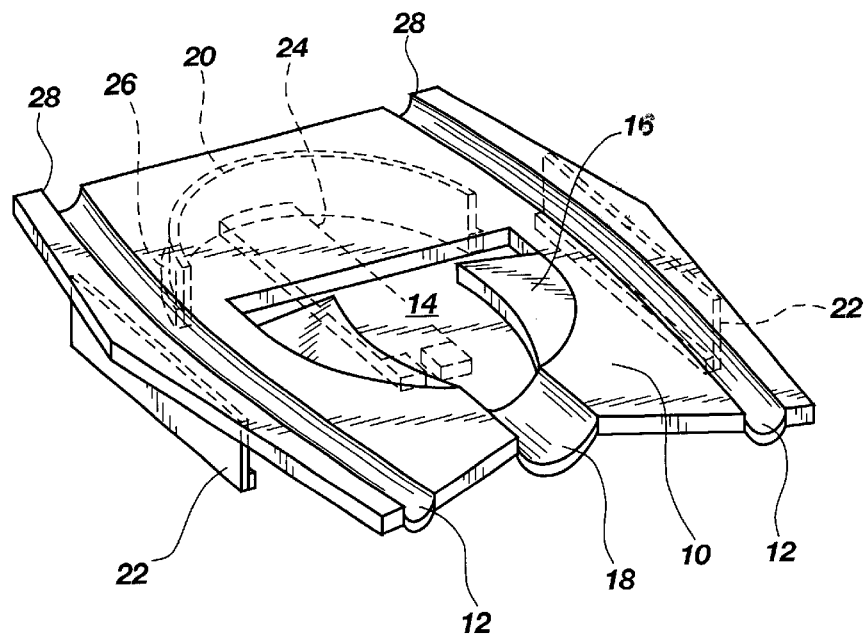
FIG. 1 shows an isometric view of the Stethoscope Carrier.
Figure 2:
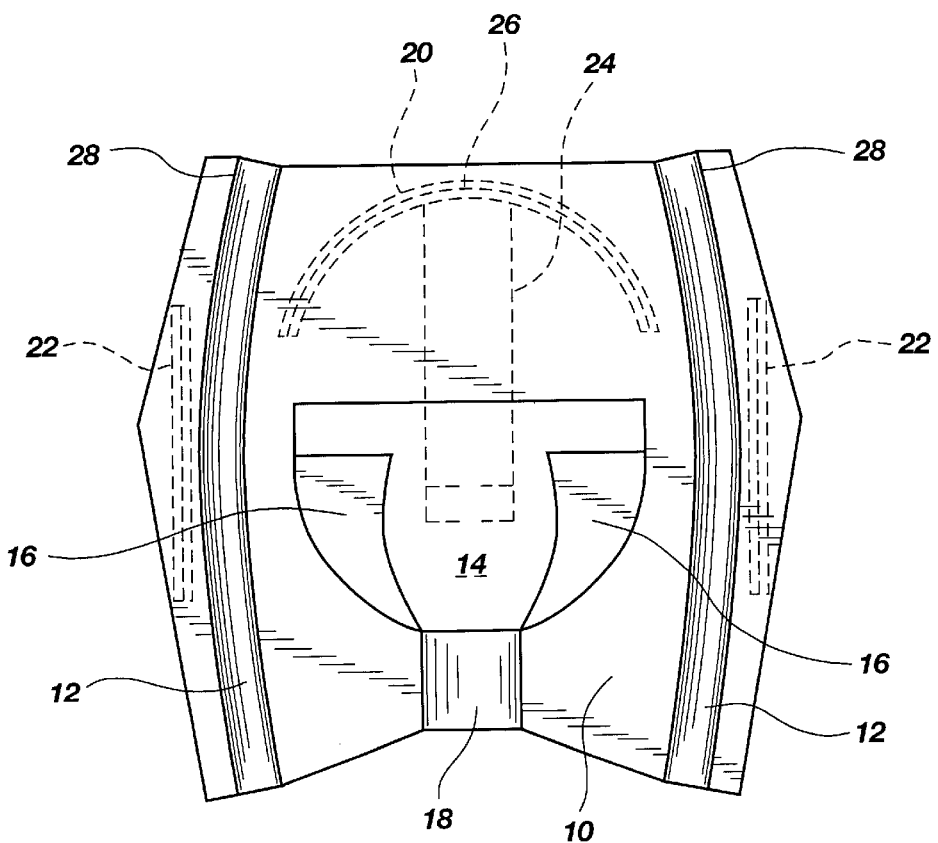
FIG. 2 provides a plan view of the Stethoscope Carrier.

In the preferred embodiment, the main body of the Stethoscope Carrier 10 is constructed from a lightweight, malleable material which is strong enough to hold the weight of a stethoscope and flexible enough to accommodate repeated insertion, retention, and removal of the stethoscope without fracturing.

Preferably, the material from which the main body of the Stethoscope Carrier 10 is manufactured is a flexible, injection-molded plastic such as polyethylene terephthalate (PET), which is commercially available from Eastman Chemical Co. of Kingsport, Tenn. However, the Stethoscope Carrier can be made of any material which can satisfy the strength, weight, and flexibility requirements discussed above. Such materials include polyethylene, polypropylene, vinyl, nylon, rubber, leather, various impregnated or laminated fibrous materials, various plasticized materials, cardboard, paper, aluminum, and carbon graphite.

Vertical ear piece retaining grooves 12 are located laterally on the front surface of the main body 10. The indentations which constitute the vertical ear piece retaining grooves 12 provide a space into which the ear pieces of a stethoscope can be clipped, behind vertical ear piece retaining groove keepers 28.

Various mechanisms can be used for attachment of the ear pieces to the main body of the Stethoscope Carrier 10. The preferred embodiment utilizes the natural springiness of the material from which the main body of the Stethoscope Carrier 10 is constructed. Other suitable mechanisms for attachment of the ear pieces include, but are not limited to VELCRO® (releasable hook and loop fasteners) adhesives, clips, bearings, and locking devices.

Centrally, on the anterior surface of the main body of the Stethoscope Carrier 10, there is an opening or orifice designated bell receiver space 14. Bell receiver space 14 allows the bell of a stethoscope to be inserted into the main body of the Stethoscope Carrier 10 and to slide downward until the neck of the stethoscope, i.e., the point where the tubing of the stethoscope attaches to the bell of the stethoscope, rests on a recessed bell retaining collar 18. The bell of the stethoscope is then behind the anterior surface of the main body of the Stethoscope Carrier 10. Two protruding bell receiver flanges 16 extending anteriorly on each side of the bell receiver space 14 allow the stethoscope bell to slide into place with ease. Bell receiver space 14, bell receiver flanges 16, and recessed bell retaining collar 18 are shown in their preferred embodiment. The shape and existence of these structures may be varied while maintaining the basic function and concept of the Stethoscope Carrier.

Once the stethoscope bell rests on the recessed bell retaining collar 18, the tubing of the stethoscope is posterior to the main body of the Stethoscope Carrier 10. This allows the user to wrap the tubing of the stethoscope upward behind a side tubing retainer 22, which side tubing retainer 22 is preferably located on the posterior surface of the main body of the Stethoscope Carrier 10; over an arched tubing shelf/retainer 20, which arched tubing shelf/retainer 20 is preferably located on the posterior surface of the main body of the Stethoscope carrier 10; and back down the opposite of the Stethoscope Carrier, once again behind the side tubing retainer 22, which side tubing retainer 22 is preferably located on the posterior surface of the main body of the Stethoscope Carrier 10 but on the opposite side of the arched tubing shelf/retainer 20 from the previously mentioned side tubing retainer 22.

To aid in tubing retention, the side tubing retainers 22 and the arched tubing shelf/retainer 20 have elevated reinforcement edges (also termed "retaining edges") 26. These accessories are shown in the preferred embodiment of the Stethoscope Carrier; the Stethoscope Carrier could, however, still be functional even if these items were discarded or altered. They serve only as a mechanism to take up slack of the stethoscope tubing.

A waist clip anchoring device 24 is positioned posteriorly to the main body of the Stethoscope Carrier 10 and attached to the central posterior aspect of the arched tubing shelf/retainer 20. The waist clip anchoring device 24, as its name implies, serves as a means of attachment or anchor to the clothing of the user. Again this is a preferred embodiment; but many different attachment methods may be employed, such as clips, pins, locks, VELCRO® (releasable hook and loop fasteners) hooks, and belt loops.

Moreover, the Stethoscope Carrier can be used in various ways.

A user could first slide a bell of a stethoscope into the bell receiver space 14 until the neck of the stethoscope rests on the recessed bell retaining collar 18. Then the tubing of the stethoscope could either be allowed to hang freely or could be wrapped around the posterior aspect of the main body of the Stethoscope Carrier 10, as previously described. Alternatively, the ear pieces of the stethoscope could be directed anteriorly to the main body of the Stethoscope Carrier 10 and clipped into the vertical ear piece retaining grooves 12 behind the vertical ear piece retaining groove keepers 28.

Once a stethoscope has been placed in the Stethoscope Carrier, the stethoscope becomes more manageable and compact. The Stethoscope Carrier, therefore, provides a convenient means for holding and transporting a stethoscope in a controlled manner, especially when used in combination with a means for anchoring the Stethoscope Carrier and, consequently, a stethoscope to an article of clothing, backpack, or other support structure.

Thus, one can see that the Stethoscope Carrier provides a highly reliable, lightweight, and strong, yet economical, means for holding and transporting a stethoscope. The Stethoscope Carrier also allows the Carrier, itself, and a stethoscope within the Carrier to be anchored securely, thereby facilitating both transportation and storage.

While the preceding description contains many specific details, these should not be construed as limitations upon the scope of the invention, but rather, as examples of one preferred embodiment thereof. Many other variations are possible. For example, as previously mentioned, the shape, material, and mechanisms of attachment may be varied. Accordingly, the scope of the invention should be determined not by the embodiment illustrated, but by the appended claims and their legal equivalents.

What is claimed is:

1. A stethoscope carrying device which comprises:

an anchoring mechanism for said stethoscope carrying device;

a means for holding and transporting a stethoscope; and a means for releasably retaining the stethoscope ear pieces.

2. A stethoscope carrying device, which comprises:

an anchoring mechanism for said stethoscope carrying device;

a means for holding and transporting a stethoscope, and a means for retaining the tubing of the stethoscope, wherein the means for retaining the tubing of the stethoscope is located posteriorly with respect to the means for holding and transporting a stethoscope.

3. A stethoscope carrying device which comprises:

an anchoring mechanism for said stethoscope carrying device;

a means for holding and transporting a stethoscope; and a set of vertical ear piece retaining grooves located laterally on said stethoscope carrying device.

4. The stethoscope carrying device as recited in claim 3, further comprising:

ear piece retaining groove keepers bordering each ear piece retaining groove to anchor the ear pieces and stethoscope securely in place.

5. A stethoscope carrying device which comprises:

an anchoring mechanism for said stethoscope carrying device;

a means for holding and transporting a stethoscope: and two side tubing retainers and an arched tubing shelf/retainer for retaining the tubing of the stethoscope.

6. The stethoscope carrying device as recited in claim 5, wherein:

the retainers are located posteriorly with respect to the means for holding and transporting a stethoscope.

7. The stethoscope carrying device as recited in claim 5, further comprising:

a set of vertical ear piece retaining grooves located laterally on said stethoscope carrying device.

8. The stethoscope carrying device as recited in claim 7, wherein:

the retainers are located posteriorly with respect to the means for holding and transporting a stethoscope.

9. The stethoscope carrying device as recited in claim 7, further comprising:

ear piece retaining groove keepers bordering each ear piece retaining groove to anchor the ear pieces and stethoscope securely in place.

10. The stethoscope carrying device as recited in claim 9, wherein:

the retainers are located posteriorly with respect to the means for holding and transporting a stethoscope.

* * * * *